(12) United States Patent
Schadewaldt et al.

(10) Patent No.: US 11,931,201 B2
(45) Date of Patent: Mar. 19, 2024

(54) DEVICE AND METHOD FOR OBTAINING ANATOMICAL MEASUREMENTS FROM AN ULTRASOUND IMAGE (71) Applicant: KONINKLIJKE PHILIPS N.V., Eindhoven (NL)

(72) Inventors: Nicole Schadewaldt, Hamburg (DE); Cristian Lorenz, Hamburg (DE); Alexander Schmidt-Richberg, Hamburg (DE); Tobias Klinder, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 905 days.

(21) Appl. No.: 16/963,680

(22) PCT Filed: Jan. 9, 2019

(86) PCT No.: PCT/EP2019/050449
§ 371 (c)(1),
(2) Date: Jul. 21, 2020

(87) PCT Pub. No.: WO2019/145147
PCT Pub. Date: Aug. 1, 2019

(65) Prior Publication Data
US 2021/0077062 A1 Mar. 18, 2021

(30) Foreign Application Priority Data
Jan. 23, 2018 (EP) .................... 18152934

(51) Int. Cl.
A61B 8/14 (2006.01)
A61B 8/00 (2006.01)
(Continued)

(52) U.S. Cl.
CPC ............ *A61B 8/0866* (2013.01); *A61B 8/463* (2013.01); *A61B 8/465* (2013.01); *A61B 8/469* (2013.01);
(Continued)

(58) Field of Classification Search
CPC ..... A61B 5/1076; A61B 8/0866; A61B 8/463; A61B 8/465; A61B 8/468; A61B 8/469;
(Continued)

(56) References Cited

U.S. PATENT DOCUMENTS 5,588,435 A 12/1996 Weng et al.
5,605,155 A 2/1997 Chalana et al.
(Continued)

FOREIGN PATENT DOCUMENTS

JP 2006271862 A 10/2006
JP 2009261800 A 11/2009
(Continued)

OTHER PUBLICATIONS

PCT/EP2019/050449 ISR & WO, dated Apr. 23, 2019, 14 Pages.
(Continued)

*Primary Examiner* — Mark D Remaly (57) ABSTRACT

The invention provides a method for making anatomical measurements using a captured ultrasound image representative of the anatomical region of interest. The method comprises receiving (20) data representative of a set of points selected by a user within the image and interpreting from the points a particular anatomical measurement type which the user is intending to perform. In particular, the points are processed to identify (24) a pattern or other geometrical characteristic of the points, and the location (22) of at least one of the points within the image is also identified. These two characteristics are used to identify from the set of points which measurement the operator is (Continued)

performing. Once the measurement is identified, an appropriate measurement template (26) is selected and applied in order to derive (30) from the set of points an anatomical measurement.

19 Claims, 3 Drawing Sheets

(51) Int. Cl.
  *A61B 8/08* (2006.01)
  *G06T 7/00* (2017.01)
  *G06T 7/62* (2017.01)

(52) U.S. Cl.
  CPC .............. *G06T 7/0012* (2013.01); *G06T 7/62* (2017.01); *G06T 2207/10132* (2013.01); *G06T 2207/20101* (2013.01); *G06T 2207/30044* (2013.01)

(58) Field of Classification Search
  CPC ........ A61B 8/5223; G06T 2207/10132; G06T 2207/20101; G06T 2207/30004; G06T 2207/30044; G06T 7/0012; G06T 7/62; G16H 30/40; G16H 40/63; G16H 50/20; G16H 50/30
  See application file for complete search history.

(56) References Cited

U.S. PATENT DOCUMENTS

| | | | |
|---|---|---|---|
| 5,997,479 | A | 12/1999 | Savord et al. |
| 6,013,032 | A | 1/2000 | Savord |
| 6,283,919 | B1 | 9/2001 | Roundhill et al. |
| 6,306,089 | B1 | 10/2001 | Coleman et al. |
| 6,443,896 | B1 | 9/2002 | Detmer |
| 6,458,083 | B1 | 10/2002 | Jago et al. |
| 6,530,885 | B1 | 3/2003 | Entrekin et al. |
| 6,623,432 | B2 | 9/2003 | Powers et al. |
| 2011/0282199 | A1 | 11/2011 | Lee et al. |
| 2015/0265247 | A1 | 9/2015 | Roh et al. |
| 2016/0085328 | A1 | 3/2016 | Lee et al. |

FOREIGN PATENT DOCUMENTS

| | | |
|---|---|---|
| JP | 2013039156 A | 2/2013 |
| NO | 2016190256 A1 | 12/2016 |
| WO | 2016042146 A1 | 3/2016 |

OTHER PUBLICATIONS

Baumgartner et al: "Real-Time Standard Scan Plane Detection and Localisation in Fetal Ultrasound Using Fully Convolutional Neural Networks"; MICCAI, 2006.

Carneiro et al: "Automatick Fetal Measurements in Ultrasound Using Constrained Probabilistic Boosting Tree": MICCAI 2007, Part II, LNCS 4792, pp. 571-579.

Carneiro et al: "Knowledge-Based Automated Fetal Biometrics"; RDMS Siemens Medical Solutions, 2000.

Keraudren et al: "Automated Localization of Fetal Organs in MRI Using Random Forests With Steerable Features"; MICCAI 2015, pp. 620-627.

Schmidt-Richberg et al: "Abdomen Segmentation in 3D Fetal Ultrasound Using CNN-Powered Deformable Models"; Infant and Ophthalmic Medical Image Analysis, FIFI 2017, Lecture Notes in Computer Science, vol. 10554.

Waechter-Stehle et al: "Learning From Redundant but Inconsistent Reference Data: Anatomical Views and Measurements for Fetal Brain Screening"; SPIE Medical Imaging, 2016, vol. 9784, pp. 97841A-1-97841A-7.

Wang et al: "Detection and Measurement of Fetal Abdominal Contour in Ultrasound Images Via Local Phase Information and Iterative Randomized Hough Transform"; Bio-Medical Materials and Engineering, vol. 24, No. 1, pp. 1261-1267, 2014.

DEVICE AND METHOD FOR OBTAINING ANATOMICAL MEASUREMENTS FROM AN ULTRASOUND IMAGE

CROSS-REFERENCE TO PRIOR APPLICATIONS

This application is the U.S. National Phase application under 35 U.S.C. § 371 of International Application No. PCT/EP2019/050449, filed on Jan. 9, 2019, which claims the benefit of European Patent Application No. 18152934.8, filed on Jan. 23, 2018. These applications are hereby incorporated by reference herein.

FIELD OF THE INVENTION

This invention relates to a method and device for obtaining anatomical measurements from an ultrasound image.

BACKGROUND OF THE INVENTION

Ultrasound imaging is widely used for investigating the health and characteristics of internal anatomical structures. It may be used for instance in investigating the heart, kidneys or lungs. As part of such investigations, it is often necessary to take measurements of investigated structures, to assist in building a clinical picture.

By way of example, ultrasonic imaging is routinely used during pregnancy to assess the development of a fetus in the mother's womb, for example to detect structural anomalies in the fetus. The traditional way for a clinician to acquire an image of each required view of the fetus is to manipulate an ultrasound probe while in acoustic contact with the abdomen of the mother until a desired anatomical orientation is in the plane of the 2D imaging probe. If multiple views are to be generated with such a procedure, there is a risk of missed abnormalities because obtaining and analyzing these views requires high skill (e.g. fetal echocardiography is very operator-dependent) whilst in addition the fetus may be moving during the procedure, requiring the clinician to reorient himself or herself with the fetus each time the fetus moves.

Of particular interest to analyze the development of the fetus are so-called biometry measurements, which are used to check if the fetus is developing correctly, e.g. within expected tolerances. There are a standard set of measurement taken on ultrasound images which include biparietal diameter (BPD), head circumference (HC), abdominal circumference (AC), femur length (FL), nuchal translucency (NT) and crown-rump-length (CRL).

In addition to reference values for certain gestational ages (GA), these parameters can be used to determine e.g. the gestational age (CRL and BPD in first trimester), or a variety of abnormalities, e.g. an unusual relation between body parts.

If an abnormality is detected, additional diagnostics can be prescribed early, to ensure adequate measures are taken in time.

When performing ultrasound screening, a standard set of these biometric measures are taken. In state of the art ultrasound systems, for each given measurement, the sonographer has to select the measurement type from a list and then follow a fixed workflow to take the measurements. Selecting the measurement activates a particular measurement tool or template which ensures mouse-clicks of the operator are correctly interpreted to define the measure. For instance, some measurements require a line to be drawn and others a circle or contour, and different measurements may need different scales. The system appropriately converts the series of points identified by the user into a measurement of the correct shape and type and then correctly labels and documents it.

This workflow is slow and tedious, as it requires the operator to select each measurement to be made from a long list before it can be performed.

There have been attempts to reduce the effort and time consumption of tool selection by providing a fixed workflow which follows a set order of measurements. This avoids the multiple mouse-clicks before each measure. However, it is highly restrictive to the sonographer and may not suit their preferences. It also fails to provide flexibility for performing additional measurements which may be clinically appropriate in given situations.

There also have been proposed fully automated procedures, wherein a fetal ultrasound image is scanned and a full set of biometric measurements are automatically identified and recorded. These may be based on segmenting the ultrasound image data for instance.

One classifier based approach for automated fetal biometry for instance, called "Auto OB", is detailed in: Carneiro G et al. (2007) Automatic Fetal Measurements in Ultrasound Using Constrained Probabilistic Boosting Tree. In: Medical Image Computing and Computer-Assisted Intervention—MICCAI 2007. Lecture Notes in Computer Science, vol 4792. Springer.

While these systems reduce workload, they suffer from lack of robustness, and are never able to achieve 100% accuracy. They often for instance require input images of a specific quality or for the images to be provided in a specific order or orientation in order for the method to work correctly. This also makes achieving regulatory approval for their use in devices very difficult, since their reliability is low.

There remains a need for improving efficiency of carrying out anatomical measurements in ultrasound images which does not impede accuracy and robustness, and also provides flexibility for the sonographer.

Document WO 2016/042146 discloses a portable ultrasound scanning device for use in veterinary applications. The device is for assisting in identifying features in captured images. A user identifies a general feature type and location within the captured image, and the device returns a fully identified feature from which physiological information pertaining to the feature can be computed.

Document US 2016/085328 discloses an ultrasound diagnostic apparatus which is aimed at remedying the problem of poor input precision when using a touch screen. A touch-screen display displays an ultrasound image of an object and receives a user touch on the image. A controller acquires a seed point from the touch, and subsequently determines shape information of the object, and using this and the seed point determines a touch point corresponding to the user touch.

Document US 2011/282199 discloses a three-dimensional ultrasound system which has a display unit to display an imaged object and a control unit which generates a figure template based on a reference location of the image selected by the control unit. The figure template is automatically adjusted to fit the reference location and used to derive measurements thereof.

Document U.S. Pat. No. 5,588,435 discloses an ultrasound imaging system for use in measuring body structures. A user inputs a general geometry feature of the body structure to be measured and the particular measurement which is to be taken and the system automatically identifies the feature in an ultrasound image and automatically calculates the measurement.

SUMMARY OF THE INVENTION

The invention is defined by the claims.

According to an aspect of the invention, there is provided a computer-implemented method for obtaining anatomical measurements in an ultrasound image, the method comprising:

receiving user input data representing a set of two or more user-selected points within the ultrasound image;

identifying within the image an anatomical region corresponding to a location of at least one of the user-selected points;

identifying a geometrical characteristic of the set of user-selected points;

selecting from a pre-stored set of measurement templates a measurement template associated with the identified anatomical region and geometrical characteristic; and deriving an anatomical measurement from the set of user-defined points, using the measurement template.

The step of selecting the measurement template preferably comprises accessing a pre-stored set of measurement templates, each measurement template in the set being associated with one or more known anatomical regions and geometrical characteristics, and selecting a measurement template associated with the identified anatomical region and geometrical characteristic.

The proposed method is based on automatically detecting from a set of points which an operator selects in an image, the particular measurement which they are intending by those points to perform.

In particular, the method is based on automatically detecting the particular measurement being performed based on the location and geometrical characteristics of the set of points selected by the operator in the image. The correct measurement tool can then be applied. This avoids the need to manually select the measurement type in advance from a long list, saving the operator time and effort.

The invention provides improved robustness over fully automated measurement methods since it still relies on a sonographer's expert input in selecting the particular series of points which define the measurement. However, it provides improved efficiency over standard approaches by not requiring the measurement type to be manually entered in advance by the operator.

The invention also provides improved flexibility over fixed workflow approaches, since the sonographer is able to decide ad hoc which measurements to do and in which order, and the method is able to response appropriately and apply the appropriate tool.

The invention hence retains the clinician's key expertise, ensuring clinical robustness, while deploying automation to speed up tasks which are merely clerical, improving efficiency.

The method may further comprise an initial step of receiving or obtaining the ultrasound image. Alternatively, the image may already be locally accessible.

The method may comprise a further step of generating output data representative of the derived measurement. The method may then comprise a further step of communicating said output data via a communication interface.

The method may further comprise labelling or tagging the measurement according to the measurement template used in deriving the measurement. This ensures all of the measurements are identifiable once they are collated and stored.

The user-input two or more points are separate points, for instance spaced from one another; i.e. they are discrete points.

The method involves identifying a geometrical characteristic of the set of user-selected points. A geometrical characteristic means in general a property pertaining to a geometry described by the set of points. Geometry may in general refer for instance to the points, lines, angles and/or figures described by or defined by the set of points.

Identifying the geometrical characteristic may comprise analyzing the image to detect or identify a geometrical characteristic pertaining to the points, e.g. a geometry embodied or described by the points.

According to one or more examples, identifying the geometrical characteristic may include identifying shape information relating to a pattern or line (or contour) described by the points. For example, detecting one or more of: whether the points describe a straight line, or a curved line or contour, whether such a line is open or closed, a particular curvature, arc or other path characteristic of such a line, whether the points describe instead a geometrical pattern, whether the points describe a combination of two lines, or a combination of a pattern and a line, or any other combination, or a shape of any such pattern.

According to one or more examples, identifying the geometrical characteristic may include identifying shape properties of a pattern or line (or contour) described by at least a subset of the points.

In examples, the geometrical characteristic may comprise a geometrical pattern in the set of points. The pattern might for instance be a geometrical shape or form described by the points such as a contour of a particular shape or a line defining a particular arc or curve.

Alternatively, the geometrical characteristic may comprise geometrical feature of the points, such as a separation between two or more of the points. A distance between two or more of the points may allow identification of the measurement being performed.

The separation may in examples be a distance measured in local image units, e.g. pixels, or true spatial units, or in units of the spatial region captured within the image.

In examples, identifying the anatomical region may comprise identifying the anatomical region corresponding to the chronologically first selected point.

Selecting of a measurement template may in examples comprise first identifying a set of measurement templates associated with the identified anatomical region and geometrical pattern, and selecting one of the set based on a user input. Selection of the measurement template in this case is not fully automatic, but significantly reduces the burden for the operator of searching through an entire list of possible measurements. The identified set of templates may typically comprise only 2-5 possibilities for instance.

Alternatively, the selecting of a measurement template may comprise first identifying a set of measurement templates associated with the identified anatomical region and geometrical pattern (as above), and selecting one of the set based on further image analysis.

In examples, determining the anatomical region may comprise performing an image segmentation procedure on the ultrasound image.

The pre-stored set of measurement templates may be stored in a database, or other data structure in particular examples.

According to one or more sets of embodiments, the method may be a fetal measurement method wherein the anatomical region is a region of a fetus captured in the image. Accordingly, the method may be a method for obtaining measurements of a fetus e.g. during fetal screening. However, the inventive concept is more broadly applicable to measurements performed on an anatomical region, in humans or animals.

In accordance with one or more sets of embodiments, the method may be a biometrical measurement method for obtaining biometric measurements. Biometrics is the technical term for body measurements and calculations. It refers to metrics related to human characteristics.

The method may in examples be for obtaining fetal biometric measurements, and optionally wherein the method is for obtaining one or more of the following measurements: biparietal diameter, BPD, head circumference, HC, abdominal circumference, AC, femur length, FL, nuchal translucency, NT, and crown-rump-length, CRL.

Where a tag or label is generated for the obtained measurement, the method may further comprise storing the obtained measurement in conjunction with the applied label or tag.

Examples in accordance with a further aspect of the invention provide a computer program means comprising computer program code adapted, when run on a computer, to perform a method in accordance any of the example methods outlined above, or any example method described in this disclosure.

Examples in accordance with a further aspect of the invention provide an image analysis device for obtaining anatomical measurements in an ultrasound image, the device comprising:

a database comprising a pre-stored set of measurement templates for use in performing different anatomical measurements; and a measurement processor configured to:
  receive user input data representing a set of user-selected points within the ultrasound image,
  identify within the image an anatomical region corresponding to a location of at least one of the user-selected points,
  identify a geometrical characteristic of the set of user-selected points,
  select from the pre-stored set of measurement templates a measurement template associated with the identified anatomical region and geometrical characteristic, and
  derive an anatomical measurement from the set of user-defined points, using the measurement template.

Each measurement template in the pre-stored set is preferably associated with one or more known anatomical regions and geometrical characteristics.

The device may in examples comprise means for performing a further step of receiving or obtaining the ultrasound image. Alternatively, the image may already be locally accessible, for instance if the device is part of an ultrasound imaging device which has been used to obtain the image.

The measurement processor may be adapted to perform a further step of generating output data representative of the derived measurement. The processor may then be adapted to perform a further step of communicating said output data via a communication interface.

The measurement processor may be any kind of processor suitable for performing the set of steps outlined above.

The device may further comprise a user interface means for use by a user in inputting the set of user-selected points within the ultrasound image. The user interface means may be a mouse or other pointer device.

The measurement processor may be configured to perform a method for obtaining anatomical measurements in an ultrasound image in accordance with any example or embodiment described in this disclosure or defined in any claim of this application.

Examples in accordance with a further aspect of the invention provide an ultrasound imaging device, comprising: one or more ultrasound imaging probes for acquiring ultrasound image data; an image processor configured to process the image data to derive an ultrasound image; and an image analysis device in accordance with any of the examples outlined above, or in accordance with any other example or embodiment described in this disclosure, adapted to obtain anatomical measurements in the derived ultrasound image.

BRIEF DESCRIPTION OF THE DRAWINGS

Examples of the invention will now be described in detail with reference to the accompanying drawings, in which.

DETAILED DESCRIPTION OF THE EMBODIMENTS

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a method for making anatomical measurements using a captured ultrasound image representative of the anatomical region of interest. The method comprises receiving data representative of a set of points selected by a user within the image and interpreting from the points a particular anatomical measurement type which the user is intending to perform. In particular, the points are processed to identify a pattern or other geometrical characteristic of the points, and the location of at least one of the points within the image is also identified. These two characteristics are used to identify from the set of points which measurement the operator is performing. Once the measurement is identified, an appropriate measurement template is selected and applied in order to derive from the set of points an anatomical measurement.

The process of taking measurements in state of the art devices involves selecting which measurement is to be taken from a list (which is typically very long), and then selecting various points within a captured ultrasound image which dimensionally or geometrically define or describe the measurement. This may for instance involve selecting end points of a line measurement, or points around the periphery of a contour. A measurement template is applied corresponding to the selected measurement type, which interprets the selected points appropriately in order to derive from them a measurement.

One area of particularly useful application for the invention is that of fetal ultrasound screening. This process requires the taking of a number of characteristic biometric measurements of the fetus, allowing its development to be checked and monitored.

Figure 1:
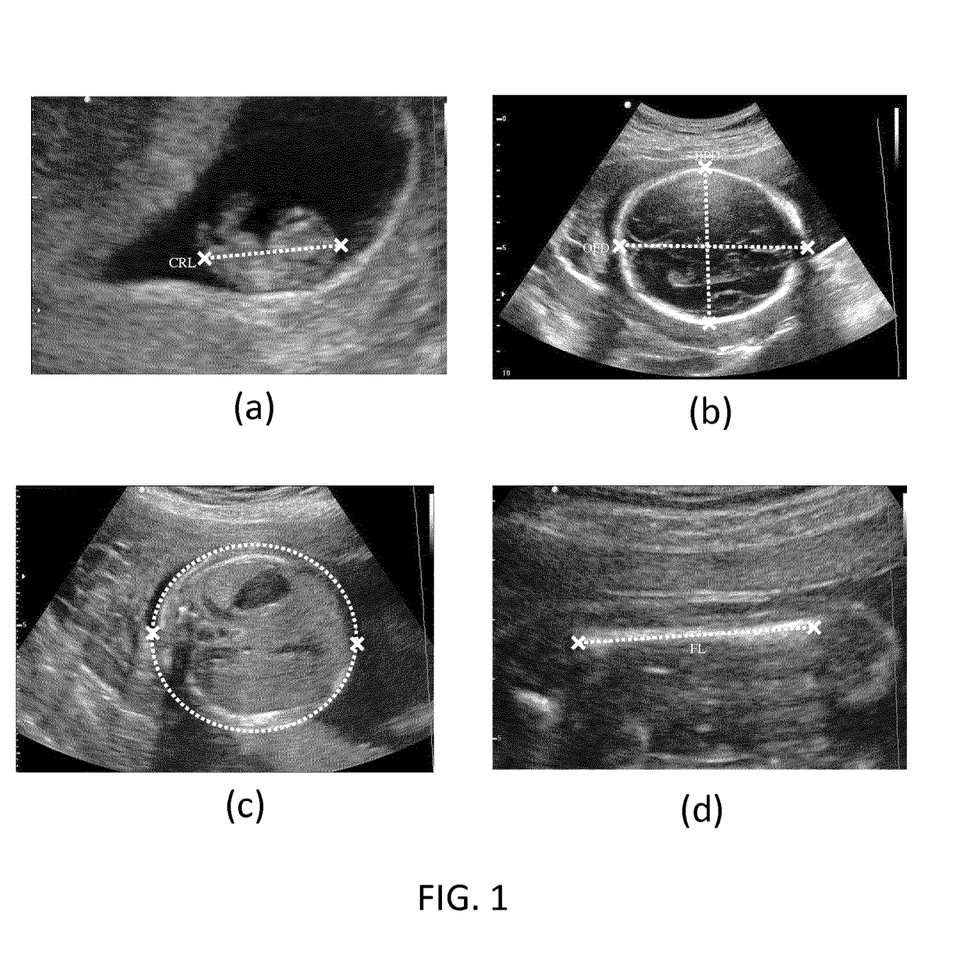
FIG. 1 shows example anatomical measurements of an ultrasound image.

FIG. 1 shows some example fetal biometric measurements. FIG. 1(a) shows a crown-rump-length (CRL) measurement, which comprises a linear extension along the length of the fetus. The measurement is taken by selecting user selecting two points (indicated by the crosses), which are interpreted by the CRL measurement template as end-points of a line. The CRL measurement template then determines and determines the CRL measurement as a length of a line extending between the two selected points.

FIG. 1(b) shows a Biparietal diameter (BPD) measurement (horizontal line) and Occipito-frontal diameter (OFD) measurement (vertical line). Each of these measurements is also performed by a user by selecting two points which are interpreted by the respective measurement templates as end points of lines.

FIG. 1(c) shows an abdominal circumference (AC) measurement. This measurement is performed by selecting at least three points around the abdominal circumference. The measurement template interprets these as points on a closed contour and interpolates a contour extending through all of the points. The length of the contour is derived, this length providing the AC measurement.

FIG. 1(d) shows a femur length (FL) measurement. This again involves the operator selecting two points, which are interpreted by the measurement template as end points of a line which define the femur length.

The method improves efficiency in the taking of anatomical measurements in captured ultrasound images by relieving the sonographer of the burden of manually selecting which measurement template is be applied before taking each measurement.

Figure 2:
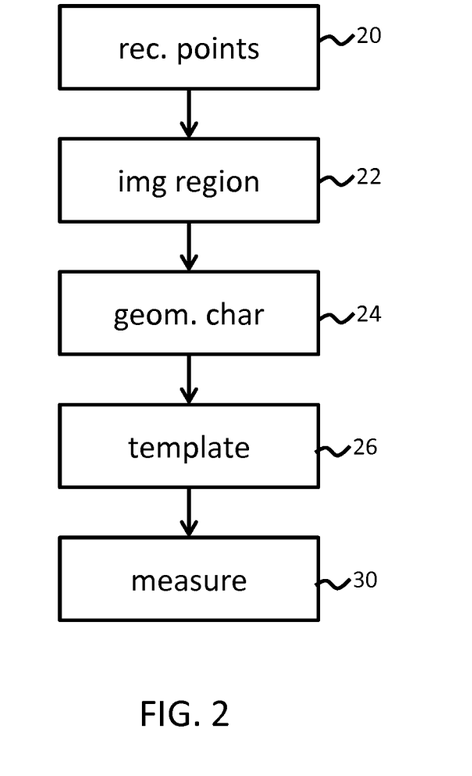
FIG. 2 shows a block diagram of an example method according to an embodiment of the invention.

An example method according to an embodiment of the present invention will now be described with reference to the block diagram of FIG. 2.

In a first step 20 ('rec. points'), user input data is received representative of a set of (at least two) points which have been selected by a user within an ultrasound image. These may be selected by a user clicking at the relevant points within the image using a mouse or other pointer device. In particular, the user may simply start to measure a biometric measurement using mouse-clicks (without selecting the measurement which is being performed). As noted above, depending on the measurement, this may be for instance two clicks (for a line, distance or diameter measurement) or several clicks (for delineation of a circumference or contour for instance).

This process of selecting the points may be performed for instance on a computer (such as a mobile computing device) or an image processing device in advance of the present method commencing. The invention is not limited to any particular input method by which the points are defined or by which the points are received. For example, although 'mouse clicks' are referred to above, this is by way of example only. Other interaction schemes to interact with the image would also be possible, e.g. Doppler recordings, or scrolling interactions, for instance to analyze heart topography.

In examples, the method may comprise an additional initial step of receiving the ultrasound image. This may in some examples comprise receiving ultrasound image data from one or more ultrasound transducer probes and processing this data to derive an image. Alternatively, it may for instance comprise receiving an already rendered image, e.g. from an image processor, or from a memory or other source where the image has been stored.

After receipt of the data representative of the set of user-selected points, a second step 22 ('img region') comprises identifying within the ultrasound image an anatomical region corresponding to a location of at least one of the user-selected points. There may be identified an anatomical region corresponding to just one of the points, e.g. just the first point, or to a plurality of points, e.g. the first point in addition to the subsequent points. The region may for instance be a region delineated or demarcated by (part or all of) the set of user-selected points. For instance the points may surround or enclose a space of a particular shape or volume, this region being identified as the anatomical region associated with the points. There may be identified a particular point associated with such an identified region, e.g. a 'center of gravity' (or centroid) point of the region.

By identifying the anatomical region in which the points have been selected, the number of possible anatomical measurements which the user could be performing is narrowed since only a certain subset will be associated to the particular region in which the user has begun to measure.

This step simply requires identification of an anatomical location in which one or more of the points has been positioned. This may be performed in examples using anatomical landmark detection: the image is analyzed or processed to identify certain landmarks or recognizable anatomical features proximal to the selected point(s) which may be used to discern a location of the point(s) in anatomical terms (their location within the anatomical region or body of interest).

By way of example, landmark detection for the particular case of fetal anatomical measurement is described in detail in Carneiro G et al. (2007) Automatic Fetal Measurements in Ultrasound Using Constrained Probabilistic Boosting Tree. In: Medical Image Computing and Computer-Assisted Intervention—MICCAI 2007. Lecture Notes in Computer Science, vol 4792. Springer.

At least partial image segmentation may be used in some examples to assist in identifying the anatomical region or location associated with one or more of the selected points. By way of example, Schmidt-Richberg A., et al (2017) "Abdomen Segmentation in 3D Fetal Ultrasound Using CNN-powered Deformable Models" In: Infant and Ophthalmic Medical Image Analysis. FIFI 2017, OMIA 2017. Lecture Notes in Computer Science, vol 10554. Springer, details fetal torso segmentation with a combination of deep learning and model based segmentation in 3D ultrasound images.

However, segmentation is not necessary for identifying the anatomical region or location associated with the user selected point(s). For example, the above-referenced paper also details a more simple region identification procedure for detecting fetal torso region. This procedure, or an analogous modification of it for other anatomical regions, may also be used for anatomical localization of points or regions, without the requirement for implementing full segmentation.

A further option for identifying the anatomical region or location associated with the point(s) is a simple view detection procedure e.g. as demonstrated in recently developed machine-learning approaches for distinguishing different standard ultrasound planes, see e.g. Christian Baumgartner et al, "Real-time Standard Scan Plane Detection and Localisation in Fetal Ultrasound using Fully Convolutional Neural Networks", MICCAI 2006.

Using these technologies, at least a general anatomical region associated with the user defined points can be identified, e.g. "longbone" or "head", which is typically sufficient for the anatomical localization necessary for embodiments of the present invention.

Additionally or alternatively, pattern matching approaches may in accordance with examples be applied to localize certain shapes within the image, e.g. round shapes or elongated shapes, which can be used to determine the anatomical region with which the one or more user-selected points are associated. Generalized Hough Transform (GHT) approaches (using template matching) may be used in examples. However, more recent machine learning approaches may instead be applied, which may outperform the classical GHT based shape localizers, as detailed for instance in W. Wang et al., "Detection and measurement of fetal abdominal contour in ultrasound images via local phase information and iterative randomized Hough transform", Biomed Mater Eng. 2014; 24(1). The random forests approach provides another machine learning approach may also be advantageously applied for facilitating shape matching in identifying the anatomical region or location. A suitable example is described in Kevin Keraudren et al., "Automated Localization of Fetal Organs in MRI Using Random Forests with Steerable Features", MICCAI 2015, pp 620-627.

After identifying the anatomical region associated with one or more of the points, a third step 24 ('geom. char') comprises identifying a geometrical characteristic of the set of user-selected points. The geometrical characteristic may comprise a (geometric) pattern described by the points or a geometric feature of the points, such a distance between two or more of the points. A pattern may for instance be a shape or figure defined by the points, e.g. a closed contour or a contour of a particular shape or outline, or a line of a particular arc or curve or length.

The geometrical characteristic may include the number of points selected, e.g. two points only might indicate a line measurement in a certain anatomical region.

More than one geometrical characteristic may be identified in some examples.

Identifying the geometrical characteristic may be performed making use of a database or datastore of known patterns and other geometrical characteristics which are associated with different anatomical measurements. This datastore or database may be specific to the particular measurement variety, e.g. fetal measurement.

Identifying the geometrical characteristic may be performed in examples using a pattern recognition algorithm, or feature recognition algorithm performed on the image. Potential patterns identified in the image may in this case be compared against different patterns stored in a database or data-store of known exemplar patterns, allowing identification of the pattern.

Suitable pattern recognition methods and approaches were described above. For example, classical Generalized Hough Transform (GHT) approaches (using template matching) may be used in examples, or more recent machine learning approaches may instead be applied, as detailed for instance in W. Wang et al., "Detection and measurement of fetal abdominal contour in ultrasound images via local phase information and iterative randomized Hough transform", Biomed Mater Eng. 2014; 24(1). The random forests approach provides another machine learning approach which may also be advantageously applied for facilitating shape matching in identifying the anatomical region or location. A suitable example is described in Kevin Keraudren et al., "Automated Localization of Fetal Organs in MRI Using Random Forests with Steerable Features", MICCAI 2015, pp 620-627.

In simplest examples, pattern recognition may comprise very simple associations, e.g. two point=line, plural points=circle/ellipse or curved line.

In accordance with one or more examples, in addition to the step of identifying a geometrical characteristic associated with one of more of the points, there may be performed a further optional step of identifying one or more properties of the underlying ultrasound image correlated with the pattern of points. For example, if the identified geometrical characteristic is that the points correspond to a line, an intensity of a corresponding line within the underlying ultrasound image may be detected. A high intensity line may provide an indication that the measurement is a typical femur measurement for instance (in particular if the identified anatomical region corresponds with a region which encompasses the femur. By way of further example, if the geometrical characteristic is that the points correspond to a round shape, e.g. as the in the case of skull or rib-cage measurement, an intensity variation around an underlying contour shape within the ultrasound image may be detected. High intensity at the sides, and/or low intensity at the front and back may provide indication that the points correspond to the skull as these are typical shading patterns associated with ultrasound images of the skull.

Following identification of the geometrical characteristic of the set of points (and optionally the additional step discussed above), a fourth step 26 ('template') comprises selecting from a pre-stored set of measurement templates a measurement template associated with the identified anatomical region and identified geometrical characteristic.

There may be stored for instance a list or database of all of the different possible measurements, and the particular geometrical characteristic(s) associated with them (as well as the anatomical region with which they are associated).

The database may for instance include data of the following form:

| Geometrical Characteristic | Measurement category | Measurement |
|---|---|---|
| 2 points | Line measurement | Femur length (FL), Humerus length (HL), crown-rump-length (CRL) |
| 2 points and a circle | Diameter | Biparietal diameter (BPD), Occipito-frontal diameter (OFD) |
| Several points defining a closed curve (e.g. a circle or ellipse). | Ellipsoid measurement | Abdominal circumference (AC), head circumference (HC) |

This data may be obtained from publicly available literature (see, e.g. https://sonoworld.com/Client/Fetus/html/appendix-03/normal_fetal_biometry/appendix-03.htm) or may be constructed from other public literature or may be constructed based on the experience of or experiments performed by sonographers.

Selecting of the correct measurement template in accordance with the fourth step 26 may in particular examples comprise the sub-steps of first ranking the possible measurement templates according to their likelihood of corresponding to the points selected by the user, and then selecting the measurement template which ranks highest (i.e. most likely).

If multiple measurements are possible for the given combination of geometrical characteristic and location, the method may in some examples comprise a further step of ranking the possible measurement templates in order of likelihood and then presenting the list to the user. One measurement template is then selected from the list based on a user input related the list, e.g. a selection of one of the templates by the user.

Presenting the list to the user may be performed using a suitable user output device, such as a display or other visual presentation device. A user input device may be used for receiving the user input indicating which measurement template of the ranked list is to be selected. The user input and output device may be integrated in a single user interface device such as a touchscreen mobile computing device for instance.

Additionally or alternatively, if multiple measurements are possible for the given combination of geometrical characteristic and location, the method may comprise a further sub-step of performing additional image analysis, for instance applying a further pattern or feature recognition algorithm, allowing further narrowing of the list of possible measurement templates. This may then allow identification of a single measurement associated with the identified geometric characteristic and location of the points, although at the cost of additional processing time and resources. The further image analysis may comprise a step as described above wherein a characteristic of the underlying ultrasound image correlated with the points is identified, e.g. an intensity characteristic.

By way of example, it may be derived that the measurement being taken by the operator is one associated with the head of a fetus captured within the ultrasound image, and comprises a line measurement. There are at least two measurements which could correspond to these properties: the Bi-parietal diameter (BPD) and the Occipito-Frontal diameter (OFD) (these are depicted as the vertical and horizontal line respectively in FIG. 1(*b*)). The method may in this case for instance comprise the further sub-step of identifying the orientation of the measurement line relative to the head, and applying this to thereby determine with which of the BPD and OFD the measurement being taken more likely corresponds.

Following selection of a measurement template, the method comprises a fifth step 30 ('measure') of deriving an anatomical measurement from the set of user-defined points, using the measurement template. In this step the selected template is applied to derive the measurement. The measurement template may comprise a measurement algorithm or rule which dictates how the selected set of points should be interpreted or processed in order to derive from them a measurement. For instance, a measurement template for an abdominal circumference measurement might comprise deriving a smooth closed contour line (for instance an ellipsoid) which connects all of the points selected by the user, and then deriving a length of the contour (a circumference) using a particular conversion metric comprised by the template (i.e. a metric allowing conversion of image-space length to actual-size lengths).

The method may comprise a further step of labelling or tagging the measurement according to the measurement template used in deriving the measurement.

The derived (and possibly tagged) measurement may in examples be communicated to a memory or data store or external computer or system. This may comprise generating output data representative of the measurement and further communicating the output data.

In addition to labelling and storing the measurement(s), the method may comprise further steps of capturing screenshots corresponding to one or more of the measurements taken, e.g. showing the points selected by the user within the image and preferably the line or contour connecting them and corresponding to the measurement taken. These may be stored or archived in addition to the measurements captured. The measurements may be labelled on the image.

The method may comprise a further step of associating the measurement with a corresponding gestational age, e.g. to determine a gestational age of the fetus. This may be based on a stored data set of standard values for the measurement for each gestational age. One or more of the obtained measurements may in examples be marked on a graph of reference values for the measurement type vs gestational age. This marked graph may be displayed to the user on a user output device and/or stored along with the obtained measurement.

Although the above example has been described in relation to the taking of biometric measurements, this is by way of example only. The method of the invention can be applied to the obtaining of any anatomical measurements from an ultrasound image. The method is also applicable to (anatomical) images obtained by other imaging modalities than ultrasound; ultrasound is one advantageous application of the method.

Example methods in accordance with the invention offer at least three main advantages compared to systems which implement fully automated measurement. First, by virtue of the fact that expert sonographer judgment is still used to mark out each measurement, the accuracy of measurements is not diminished compared to the standard approach of selecting the measurement being performed in advance of each measurement. Consequently, it is much easier to get regulatory approval for a device implementing the method (e.g. from the US Food and Drug Administration).

Secondly, in contrast to fully automated methods, examples of the present invention allow a sonographer to take measurements in any arbitrary order, affording greater flexibility.

Thirdly, the method is easily extensible to the inclusion of new measurements. This would require simply adding the new measurement to the list along with e.g. an associated geometric characteristic and anatomical location which can be used to identify the measurement. In a simplest example, the additional measurement may be added with only a basic geometric characterization, e.g. that the measurement is a line measurement identified by two points, in addition to an anatomical region. In use, the measurement may then appear as one of a list of possible line measurements for a line drawn in the anatomical region. As described above, this list may be presented to the user to select the appropriate measurement, or further image analysis may be performed in an attempt to rule in or out other (more precisely defined) measurements in the list.

Embodiments of the present method may be applied to obtaining measurements from ultrasound images. This includes both 2D and 3D ultrasound images. Segmentation may in some examples be used in identifying an anatomical location of the points in 3D images; a classification approach might for example be used in identifying an anatomical location of the points in 2D images.

Any method according to the present invention may be implemented using an image analysis device comprising a measurement processor adapted to carry out the method.

Accordingly, a further aspect of the invention provides an image analysis device for obtaining anatomical measurements in an ultrasound image, the device comprising: a database comprising a pre-stored set of measurement templates for use in performing different anatomical measurements; and a measurement processor configured to:
  receive user input data representing a set of user-selected points within the ultrasound image,
  identify within the image an anatomical region corresponding to a location of one of the user-selected points,
  identify a geometrical characteristic of the set of user-selected points,
  select from the pre-stored set of measurement templates a measurement template associated with the identified anatomical region and geometrical characteristic, and
  derive an anatomical measurement from the set of user-defined points, using the measurement template.

The measurement processor may be any kind of processor suitable for performing the set of steps outlined above.

In some examples, the device may further comprise a user interface means for use by a user in inputting the set of user-selected points within the ultrasound image. The user interface means may by way of particular example comprise a mouse or other pointer device.

As noted above, in accordance with one or more examples, the ultrasound image from which the measurements are obtained may be acquired using an ultrasound imaging device.

Accordingly, a further aspect of the invention provides an ultrasound imaging device comprising one or more ultrasound imaging probes and an image analysis device as described above. An example is schematically depicted in block diagram form in FIG. 3.

Figure 3:
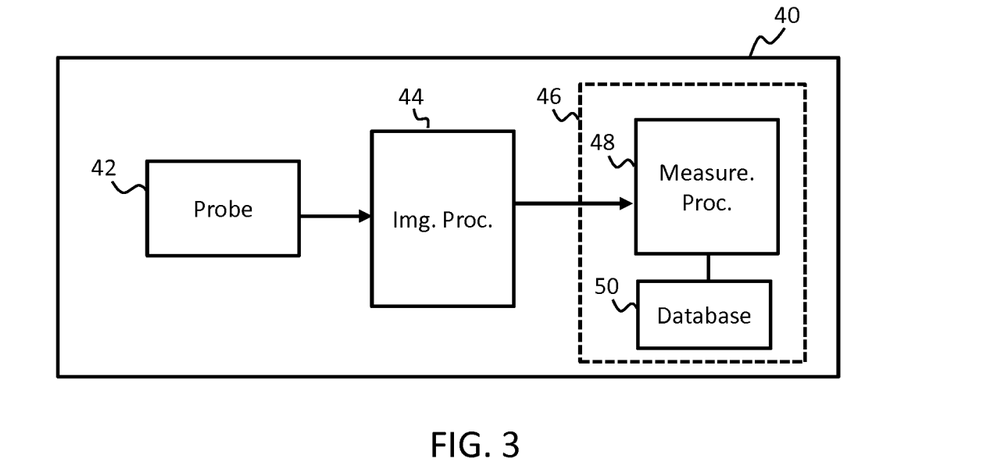
FIG. 3 shows an example ultrasound imaging device in accordance with an embodiment of the invention.

The ultrasound imaging device 40 comprises one or more ultrasound imaging probes 42 for acquiring ultrasound image data. FIG. 3 shows just one probe 42 for illustration. The probe comprises an ultrasound transducer arrangement, comprising at least one transducer and preferably comprising a transducer array. The transducer array may be steerable for instance by means of beamforming performed by the device.

The ultrasound imaging probe 42 is communicatively coupled with an image processor 44. The image processor is configured to process image data acquired by the probe 42 to thereby derive one or more ultrasound images.

An image analysis device 46 in accordance with any of the examples or embodiments described above, comprising a measurement processor 48 and a database 50 storing measurement templates, is further provided, operatively coupled to the image processor 44 for receiving the image(s) generated by the image processor. The image analysis device 46 is adapted to process the derived ultrasound image(s) (in accordance with the steps discussed in any of the examples and embodiments described above) to thereby obtain anatomical measurements in the derived ultrasound image.

The measurement processor 48 and image processor 44 may each make use of a separate processor or their functions may be performed by a same single processor. In each case, either processor may employ one or more microprocessors that may be programmed using software (e.g., microcode) to perform the required functions. By way of alternative, a controller might instead be used to perform the function of either processor, the controller implemented using hardware (e.g. circuitry). A controller might also be implemented as a combination of dedicated hardware to perform some functions and a processor (e.g., one or more programmed microprocessors and associated circuitry) to perform other functions.

Examples of processor components that may be employed in various embodiments of the present disclosure include, but are not limited to, conventional microprocessors, application specific integrated circuits (ASICs), and field-programmable gate arrays (FPGAs).

In various implementations, a processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Figure 4:
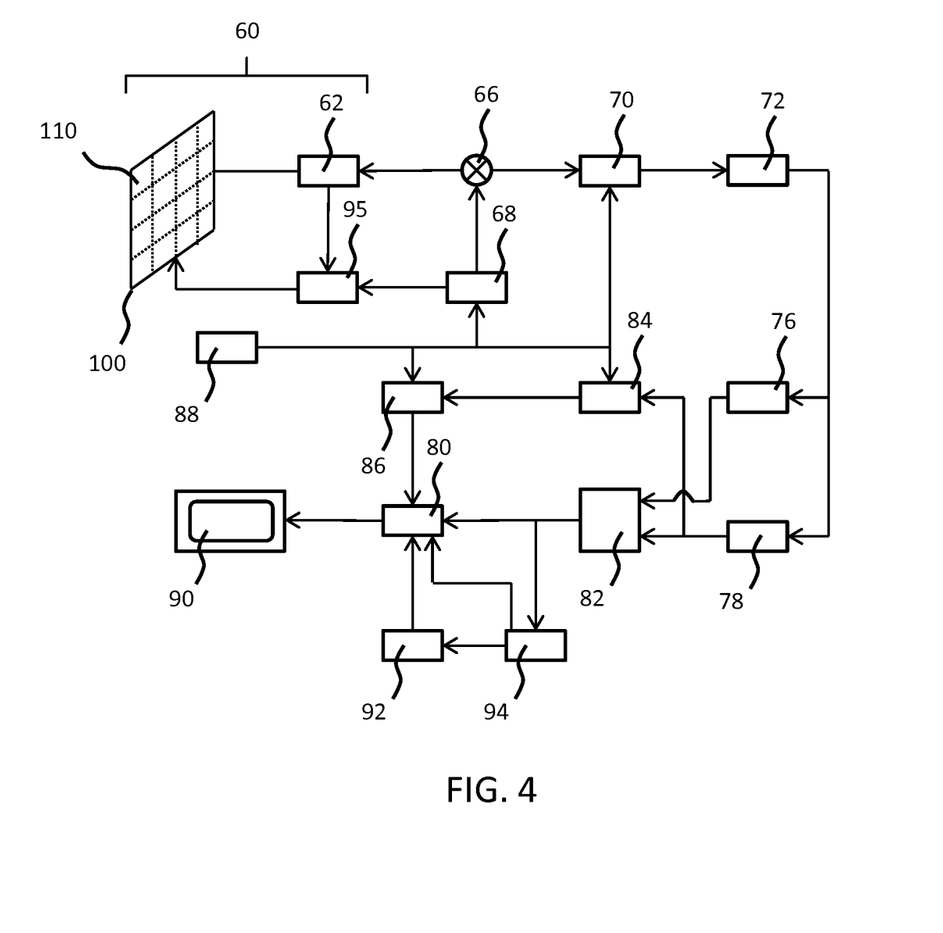
FIG. 4 shows an example ultrasound system in accordance with an embodiment.

FIG. 4 illustrates in more detail an example ultrasound system which may in examples be used to implement the probe 42 and image processor 44 parts of the ultrasound imaging device 40 of FIG. 3.

The exemplary system comprises an array transducer probe 60 which has a CMUT transducer array 100 for transmitting ultrasound waves and receiving echo information. The transducer array 100 may alternatively comprise piezoelectric transducers formed of materials such as PZT or PVDF. The transducer array 100 is a two-dimensional array of transducers 110 capable of scanning in a 2D plane or in three dimensions for 3D imaging. In another example, the transducer array may be a 1D array.

The transducer array 100 is coupled to a microbeamformer 62 in the probe which controls reception of signals by the CMUT array cells or piezoelectric elements. Microbeamformers are capable of at least partial beamforming of the signals received by sub-arrays (or "groups" or "patches") of transducers as described in U.S. Pat. No. 5,997,479 (Savord et al.), U.S. Pat. No. 6,013,032 (Savord), and U.S. Pat. No. 6,623,432 (Powers et al.).

Note that the microbeamformer is entirely optional. The examples below assume no analog beamforming.

The microbeamformer 62 is coupled by the probe cable to a transmit/receive (T/R) switch 66 which switches between transmission and reception and protects the main beamformer 70 from high energy transmit signals when a microbeamformer is not used and the transducer array is operated directly by the main system beamformer. The transmission of ultrasound beams from the transducer array 60 is directed by a transducer controller 68 coupled to the microbeamformer by the T/R switch 66 and a main transmission beamformer (not shown), which receives input from the user's operation of the user interface or control panel 88.

One of the functions controlled by the transducer controller 68 is the direction in which beams are steered and focused. Beams may be steered straight ahead from (orthogonal to) the transducer array, or at different angles for a wider field of view. The transducer controller 68 can be coupled to control a DC bias control 95 for the CMUT array. The DC bias control 95 sets DC bias voltage(s) that are applied to the CMUT cells.

In the reception channel, partially beamformed signals are produced by the microbeamformer 62 and are coupled to a main receive beamformer 70 where the partially beamformed signals from individual patches of transducers are combined into a fully beamformed signal. For example, the main beamformer 70 may have 128 channels, each of which receives a partially beamformed signal from a patch of dozens or hundreds of CMUT transducer cells or piezoelectric elements. In this way the signals received by thousands of transducers of a transducer array can contribute efficiently to a single beamformed signal.

The beamformed reception signals are coupled to a signal processor 72. The signal processor 72 can process the received echo signals in various ways, such as band-pass filtering, decimation, I and Q component separation, and harmonic signal separation which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting the noise at higher frequencies from greater depths where these frequencies are devoid of anatomical information.

The beamformers for transmission and for reception are implemented in different hardware and can have different functions. Of course, the receiver beamformer is designed to take into account the characteristics of the transmission beamformer. In FIG. 4 only the receiver beamformers 62, 70 are shown, for simplicity. In the complete system, there will also be a transmission chain with a transmission micro beamformer, and a main transmission beamformer.

The function of the micro beamformer 62 is to provide an initial combination of signals in order to decrease the number of analog signal paths. This is typically performed in the analog domain.

The final beamforming is done in the main beamformer 70 and is typically after digitization.

The transmission and reception channels use the same transducer array 60' which has a fixed frequency band. However, the bandwidth that the transmission pulses occupy can vary depending on the transmission beamforming that has been used. The reception channel can capture the whole transducer bandwidth (which is the classic approach) or by using bandpass processing it can extract only the bandwidth that contains the useful information (e.g. the harmonics of the main harmonic).

The processed signals are coupled to a B mode (i.e. brightness mode, or 2D imaging mode) processor 76 and a Doppler processor 78. The B mode processor 76 employs detection of an amplitude of the received ultrasound signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.) The Doppler processor 78 processes temporally distinct signals from tissue movement and blood flow for the detection of the motion of substances such as the flow of blood cells in the image field. The Doppler processor 78 typically includes a wall filter with parameters which may be set to pass and/or reject echoes returned from selected types of materials in the body.

The structural and motion signals produced by the B mode and Doppler processors are coupled to a scan converter 82 and a multi-planar reformatter 94. The scan converter 82 arranges the echo signals in the spatial relationship from which they were received in a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field with their Doppler-estimated velocities to produce a color Doppler image which depicts the motion of tissue and blood flow in the image field. The multi-planar reformatter will convert echoes which are received from points in a common plane in a volumetric region of the body into an ultrasound image of that plane, as described in U.S. Pat. No. 6,443,896 (Detmer). A volume renderer 92 converts the echo signals of a 3D data set into a projected 3D image as viewed from a given reference point as described in U.S. Pat. No. 6,530,885 (Entrekin et al.).

The 2D or 3D images are coupled from the scan converter 82, multi-planar reformatter 94, and volume renderer 92 to an image processor 80 for further enhancement, buffering and temporary storage for display on an image display 90. The image display may be part of a user interface 88, permitting the user (sonographer) to select the points within the image for definition of the measurements to be taken. Alternatively, inputting the user-selected points may be facilitated by a user interface means comprised by the image analysis device 46 of the ultrasound imaging device 40.

In addition to being used for imaging, the blood flow values produced by the Doppler processor 78 and tissue structure information produced by the B mode processor 76 may be coupled to a quantification processor 84. The quantification processor produces measures of different flow conditions such as the volume rate of blood flow as well as structural measurements such as the sizes of organs and gestational age. The quantification processor may receive input from the user control panel 88, such as the point in the anatomy of an image where a measurement is to be made. Output data from the quantification processor is coupled to a graphics processor 86 for the reproduction of measurement graphics and values with the image on the display 90, and for audio output from the display device 90.

The graphics processor 86 may also generate graphic overlays for display with the ultrasound images. These graphic overlays can contain standard identifying information such as patient name, date and time of the image, imaging parameters, and the like. For these purposes, the graphics processor may receive input from the user interface 88, such as patient name. The user interface is also coupled to the transmit controller 68 to control the generation of ultrasound signals from the transducer array 60' and hence the images produced by the transducer array and the ultrasound system. The transmit control function of the controller 68 is only one of the functions performed. The controller 68 also takes account of the mode of operation (given by the user) and the corresponding required transmitter configuration and band-pass configuration in the receiver analog to digital converter. The controller 68 can be a state machine with fixed states.

As noted, the above-described example ultrasound system may implement the probe 42 and image processor 44 parts of the ultrasound imaging device 40 of FIG. 3. Accordingly, referring to FIG. 3, once the image(s) have been rendered, they are communicated to the image analysis device 46. The image analysis device 46 may comprise a user interface means for facilitating input by a user of the user-selected points within the image. The rendered image (and the input user-selected points) may then be communicated to the measurement processor 48 of the image analysis device 46 for deriving the anatomical measurement(s). Alternatively, as discussed above, the ultrasound system implementing the image processor 44 may comprise a user interface 88 permitting input of the user-selected points. In this case, the image processor may output the rendered image, in addition to the user-selected points directly to the measurement processor 48 of the image analysis device 6.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A computer-implemented method for obtaining anatomical measurements in an ultrasound image, the method comprising:
   receiving user input data representing a set of user-selected points within the ultrasound image, wherein the set of user-selected points comprises two or more user-selected points;
   identifying, within the ultrasound image, an anatomical region corresponding to a location of at least one of the set of user-selected points;
   identifying a geometrical characteristic of the set of user-selected points;
   accessing a pre-stored set of measurement templates, each measurement template in the pre-stored set of measurement templates being associated with one or more known anatomical regions and geometrical characteristics;
   selecting a measurement template associated with the identified anatomical region and geometrical characteristic; and
   deriving an anatomical measurement from the set of user-defined points, using the measurement template,
   wherein identifying the geometrical characteristic includes identifying shape information relating to a line or pattern described by at least a subset of the set of user-selected points such that the shape information is distinct from the location of the at least one of the set of user-selected points.

2. A method as claimed in claim 1, further comprising labelling or tagging the anatomical measurement according to the measurement template used in deriving the anatomical measurement.

3. A method as claimed in claim 2, wherein the method further comprises storing the anatomical measurement in conjunction with the label or tag.

4. The method as claimed in claim 3, further comprising:
   capturing a screenshot associated with the anatomical measurement; and
   storing the screenshot.

5. A method as claimed in claim 1, wherein the geometrical characteristic comprises a geometrical pattern in the set of user-selected points or a geometrical feature of the set of user-selected points.

6. A method as claimed in claim 5, wherein the geometrical feature comprises a separation between two of the set of user-selected points.

7. A method as claimed in claim 1, wherein selecting the measurement template comprises:
   identifying a subset of the pre-stored set of measurement templates associated with the identified anatomical region and geometrical pattern; and
   selecting one of the subset of the pre-stored set of measurement templates based on a user input.

8. A method as claimed in claim 1, wherein determining the anatomical region comprises performing an image segmentation procedure on the ultrasound image.

9. A method as claimed in claim 1, wherein the anatomical region is a region of a fetus captured in the ultrasound image.

10. A method as claimed in claim 1, wherein the anatomical measurement comprises a biometric measurement.

11. A method as claimed in claim 10, wherein the biometric measurement comprises a fetal biometric measurement.

12. A method as claimed in claim 11, wherein fetal biometric measurement comprises at least one of biparietal diameter (BPD), head circumference (HC), abdominal circumference (AC), femur length (FL), nuchal translucency (NT), or crown-rump-length (CRL).

13. The method as claimed in claim 11, wherein the user input data representing the set of user-selected points is received without receiving a user selection associated with the measurement template.

14. The method as claimed in claim 1, further comprising:
   determining a gestational age based on the anatomical measurement; and
   displaying the gestational age.

15. The method as claimed in claim 1, further comprising: displaying the anatomical measurement.

16. A non-transitory computer-readable storage medium comprising computer program code adapted, when run on a computer, to perform the method of claim 1.

17. An image analysis device for obtaining anatomical measurements in an ultrasound image, the device comprising:
   a database comprising a pre-stored set of measurement templates for use in performing different anatomical measurements, each measurement template in the pre-stored set of measurement templates associated with one or more known anatomical regions and geometrical characteristics; and
   a measurement processor configured to:
      receive user input data representing a set of user-selected points within the ultrasound image, wherein the set of user-selected points comprises two or more user-selected points;
      identify, within the ultrasound image, an anatomical region corresponding to a location of at least one of the set of user-selected points;
      identify a geometrical characteristic of the set of user-selected points;
      select, from the pre-stored set of measurement templates, a measurement template associated with the identified anatomical region and geometrical characteristic; and
      derive an anatomical measurement from the set of user-defined points, using the measurement template,
   wherein the identification of the geometrical characteristic includes identification of shape information relating to a line or pattern described by at least a subset of the set of user-selected points such that the shape information is distinct from the location of the at least one of the user-selected points.

18. An image analysis device as claimed in claim 17, further comprising a user interface for use by a user in inputting the set of user-selected points within the ultrasound image.

19. An ultrasound imaging device, comprising:
- one or more ultrasound imaging probes for acquiring ultrasound image data;
- an image processor configured to process the image data to derive the ultrasound image; and
- an image analysis device according to claim 17.

* * * * *